(12) United States Patent
Holzhauer

(10) Patent No.: US 6,746,243 B1
(45) Date of Patent: Jun. 8, 2004

(54) ORTHODONTIC LIGATURE AND METHOD OF USE

(76) Inventor: Daniel A. Holzhauer, N. 47 W. 22175 Weyer Rd., Pewaukee, WI (US) 53072

( * ) Notice: Subject to any disclaimer, the term of this patent is extended or adjusted under 35 U.S.C. 154(b) by 0 days.

(21) Appl. No.: 10/449,356

(22) Filed: May 31, 2003

(51) Int. Cl.$^7$ .................................................. A61C 7/00
(52) U.S. Cl. ............................. 433/15; 433/11; 433/18
(58) Field of Search ............................... 433/11, 10, 15, 433/13, 18, 19

(56) References Cited

U.S. PATENT DOCUMENTS

| | | | |
|---|---|---|---|
| 2,767,469 A | 10/1956 | Gladstone | |
| 3,686,758 A | 8/1972 | Kesling | |
| 3,879,850 A | 4/1975 | Wallshein | |
| 4,054,997 A | 10/1977 | Wallshein | |
| 4,382,782 A | 5/1983 | Klein et al. | |
| 4,522,590 A | * 6/1985 | Pletcher | ........................ 433/15 |
| 4,900,250 A | 2/1990 | Kesling et al. | |
| 4,950,158 A | 8/1990 | Barngrover et al. | |
| 5,018,259 A | 5/1991 | Wildman | |
| 5,037,297 A | 8/1991 | Lerner | |
| 5,044,946 A | 9/1991 | Cleary | |
| 5,356,288 A | 10/1994 | Cohen | |
| 5,829,974 A | 11/1998 | Brosius | |

* cited by examiner

Primary Examiner—Cary E. O'Connor
(74) Attorney, Agent, or Firm—Boyle Fredrickson Newholm Stein & Gratz, S.C.

(57) ABSTRACT

A generally elastic orthodontic ligature in the shape of an O-ring is provided with a semi-rigid retaining arm for the general purpose of attaching a rubber band between teeth. The retaining arm is integral with the O-ring although the two may be made of different materials. The O-ring may have projections therein for preventing rotation of the ligature during use, and the projections may include unidirectional barbs. Further, variations in the angle or shape of the arm may be provided as desired.

26 Claims, 3 Drawing Sheets

ORTHODONTIC LIGATURE AND METHOD OF USE

BACKGROUND OF THE INVENTION

1. Field of the Invention

The present invention relates in general to the field of orthodontic ligatures. More particularly, the present invention relates to a ligature that incorporates an arm for connecting two or more ligatures with orthodontic rubber bands as needed for successful treatment.

2. Discussion of the Related Art

It is known in the prior art to attach brackets to a series of teeth, place an archwire through the brackets, and hold the archwire in place within the brackets with a ligature, often comprising a small rubber O-ring. A well-known O-ring of this type is made by 3M™ Unitek under the trade name AlastiK™.

As is known to those skilled in the art, it is often the case that intraoral force must be applied to move a tooth or teeth into a proper position. Thus, a previously recognized problem has been that of providing connection points on the brackets or archwire for attaching an elastic band therebetween. Needless to say, it is desirable to provide such a connection point easily, removably, and without patient discomfort.

What is needed therefore is a connection point that is readily attached to and removed from the bracket. Further, what is also needed is a connection point that is soft against the inner lip of the patient. Heretofore these requirements have not been fully met.

One unsatisfactory previously recognized approach involves crimping and/or welding a metal hook to the archwire. Another unsatisfactory approach involves tying a wire hook, known as a "Kobayashi hook", to the bracket. Yet another solution that has been tried is the attachment of a metal hook to the bracket, either prior to attaching the bracket to the tooth or by welding onto an existing bracket. Each of these solutions suffers from one or more problems.

Crimping a hook to an archwire is not terribly time consuming, but crimped hooks have a tendency to shift during treatment, becoming less and less effective and sometimes even becoming counterproductive. To prevent shifting around the archwire, the crimped hook can be welded into place, but this process is time consuming and uncomfortable for the patient.

The "Kobayashi hook" is a ligature wire with a shaped hook end. In systems utilizing elastic ligatures, at least the locations where the hooks are desired will have to be wire tied instead. The use of a Kobayashi hook not only introduces a different type of tie into an elastic ligature system, which increases the labor involved, but it also introduces a wire hook that is unpleasant to the patient.

Attaching a metal hook to the bracket, either before or after placement on the tooth, is also problematic. This previously recognized approach can be time consuming to implement and bothersome to the patient. In addition, it has the disadvantage of being difficult to remove once proper positioning of the teeth at issue has been achieved, requiring another time consuming and bothersome procedure.

As a result of the tedious process required to apply these solutions, none of these previously recognized systems is cost-effective, and none adds to the patient's comfort and satisfaction with the process of orthodontics. Orthodontics is a competitive business, and a preferred solution will be seen by the orthodontist as being a cost effective addition to a practice in which it is desirable to treat a maximum number of patients in a minimum amount of time. In addition, patient referral plays a large role in the practice of orthodontics. Satisfied patients are more likely to refer family members, friends, neighbors, and other associates when they have had positive orthodontic experience. Thus, a preferred solution will also minimize patient discomfort and decrease patient waiting time, both in the waiting room and in the dentist's chair.

SUMMARY AND OBJECTS OF THE INVENTION

By way of summary, the present invention is directed to a preferably elastic ligature having an integral retaining arm and a method for using the same. An effect of the present invention is to facilitate an orthodontist's ability to easily attach a rubber band between two or more teeth. A primary object of the invention is to provide an apparatus that is easy to attach and remove. Another object of the invention is to provide an apparatus that is comfortable to the wearer, thereby decreasing patient irritation.

In accordance with a first aspect of the invention, these objects are achieved by providing an apparatus comprising an elastic ligature with an integral, semi-rigid retaining arm. In one embodiment, the ligature is provided with projections for holding it in place during treatment. In another embodiment, the retaining arm is provided with a head for further retaining ability. In yet another embodiment, the retaining arm is angled for better retaining ability and/or added comfort.

In accordance with a second aspect of the invention, these objects are achieved by providing a method comprising attachment of a ligature having an integral retaining arm using the same tools required for attachment of a standard elastic ligature.

These, and other, aspects and objects of the present invention will be better appreciated and understood when considered in conjunction with the following description and the accompanying drawings. It should be understood, however, that the following description, while indicating preferred embodiments of the present invention, is given by way of illustration and not of limitation. Many changes and modifications may be made within the scope of the present invention without departing from the spirit thereof, and the invention includes all such modifications.

BRIEF DESCRIPTION OF THE DRAWINGS

A clear conception of the advantages and features constituting the present invention, and of the construction and operation of typical mechanisms provided with the present invention, will become more readily apparent by referring to the exemplary, and therefore non-limiting, embodiments illustrated in the drawings accompanying and forming a part of this specification, wherein like reference numerals designate the same elements in the several views, and in which.

Figure 1:
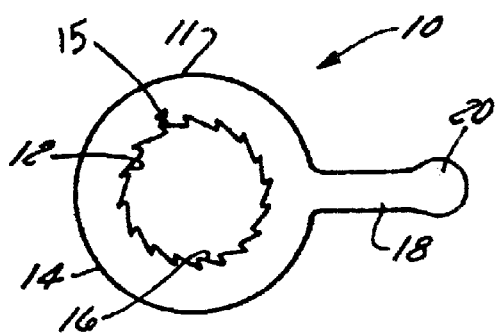
FIG. 1 illustrates a side view of a first embodiment of the invention.

In describing the preferred embodiments of the invention, which are illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose. For example, the word "connected" or terms similar thereto are often used. They are not limited to direct connection but include connection through other elements where such connection is recognized as being equivalent by those skilled in the art.

DESCRIPTION OF PREFERRED EMBODIMENTS

The present invention and the various features and advantageous details thereof are explained more fully with reference to the non-limiting embodiments described in detail in the following description.

1. System Overview

An elastic ligature for affixing an archwire to an orthodontic bracket in an orthodontic assembly is disclosed. The ligature includes an O-ring portion, or body, which has an interior portion and an exterior portion. The exterior portion has a retaining arm projecting from it, while the interior portion includes a projection or series of projections designed to keep the O-ring from rotating.

The retaining arm can be angled or shaped in a variety of ways to best facilitate orthodontic treatment, including angling the arm within the plane of the body, angling the arm away from the plane of the body, introducing a curve into the arm.

The body of the ligature is elastomeric in order to be stretched over a bracket and hold an archwire in place, but the arm of the ligature is at least somewhat rigid in order to hold an end of an elastic connector band to a retaining arm of a ligature body on another tooth bracket.

2. Detailed Description of Preferred Embodiments

Figure 2:
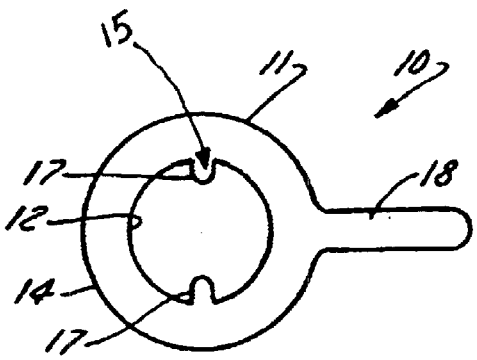
FIG. 2 illustrates a side view of a second embodiment of the invention.

As seen in FIGS. 1 and 2, ligature 10 generally consists of an O-shaped body or O-ring 11 having an interior inner portion 12 and an exterior outer portion 14. Inner portion 12 may be provided with projections 15. Projections 15 may consists of a series of unidirectional barbs 16, as shown in FIG. 1, a pair of nodules 17 as shown in FIG. 2, or any other suitable projections for preventing rotation of the ligature 10 about a bracket during use. A projecting retaining arm 18 is provided on the outer portion 14 of the O-ring 11, and the retaining arm 18 may be provided with a retaining head 20 as seen mi FIG. 1. The "simple" arm 18 shown in FIG. 1 is a generally cylindrical, while the "compound" arm 18 shown in FIG. 2 further includes a generally spherical head at its distal end.

Figure 5:
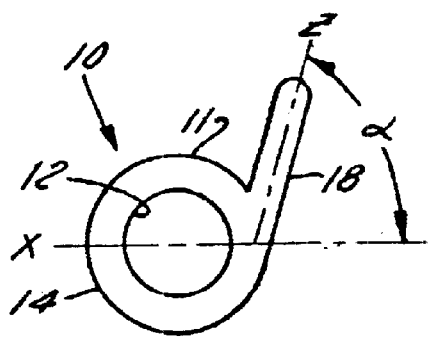
FIG. 5 illustrates a side view of yet another embodiment of the invention.
Figure 6:
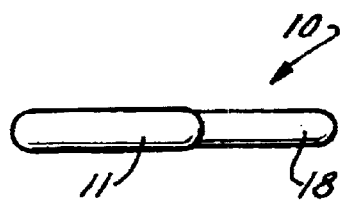
FIG. 6 illustrates a top view of the embodiment shown in FIG. 5.

Turning now to FIGS. 5–9, additional embodiments of the invention are shown in which the arm 18 extends from the exterior portion 14 of the body 11 at an angle relative to the axis x and/or plane p of the body 11. In FIG. 5, the retaining arm 18 of the ligature 10 is not located on the axis x indicated by dashed lines, but instead, arm 18 intersects the axis at line z, creating angle α. Angle α in one embodiment is preferably 90°. As shown in FIG. 6, however, the ligature 10 retains its flat profile, since the arm 18 is not angled relative to the plane p of the body 11, only to the axis x of the body 11.

Figure 7:
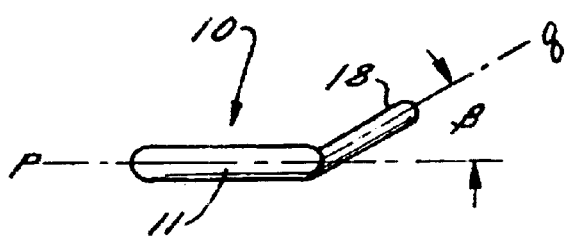
FIG. 7 illustrates a top view of still another embodiment of the invention.

FIG. 7 illustrates another embodiment in which the arm 18 is angled, this time in a direction away from the plane p of the body 11. In this embodiment, arm 18 intersects the plane p along line q, creating angle β. Naturally, arm 18 could be angled so that it is both non-planar and non-axial. While the degree of angles α and β can vary widely, limited only by the ability of ligature 10 to perform in an effective and preferred manner, in one preferred embodiment angles α and β are greater than 90°.

Figure 8:
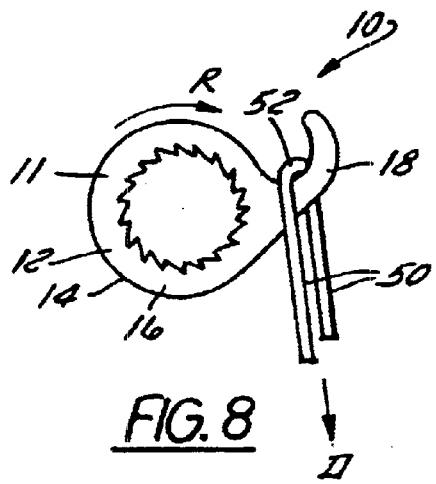
FIG. 8 illustrates a side view of a further embodiment of the invention.

In addition, arm 18 need not be a straight piece, but could be shaped in any number of ways to improve the ability of the ligature 10 to hold an elastic band 50 in specific applications. For instance, FIG. 8 shows an embodiment in which arm 18 is fashioned in a hook shape, which could extend in any direction convenient for orthodontic purposes, for retaining an end 52 of elastic band 50. Elastic band 50 pulls in direction D as shown and thus barbs 16 are shown as tightening against the rotational pull R of the elastic band 50.

Figure 9:
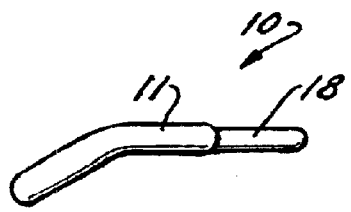
FIG. 9 illustrates yet another embodiment of the present invention.

Further, the body 11 of the ligature 10 need not necessarily be formed flat, but may also be angled as seen in FIG. 9, or may be created in a square shape rather than following the traditional O-ring format. These embodiments may aid in placement or removal of the ligature 10 from the orthodontic system, better retention of the archwire in an orthodontic system, or any of a variety of effects that may be desired. The embodiments shown and described are representative of the variations that could be introduced, but are not meant to limit the invention. It is contemplated that simpler shapes, such as a body 11 in the shape of an O and a generally straight arm 18 will be less expensive to tool and manufacture, which is why emphasis has been placed on those variations in the drawings and within this description.

Figure 10:
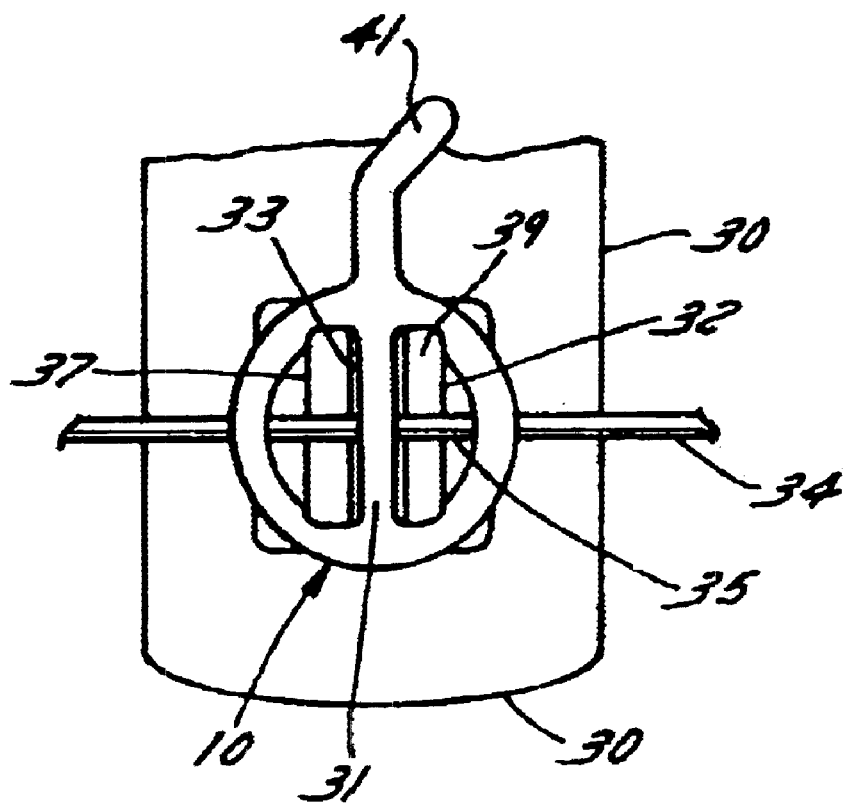
FIG. 10 illustrates still yet another embodiment of the invention.

FIG. 10 shows an elastic O-ring ligature 10 having a bar-like member 31. The bar-like member 31 is preferably integral with arm 18 and extends through the middle of the round ring. When integral, it appears that the member 31 merely juts out one side of the ring forming the arm 18. When used on a tooth (here the upper teeth), this bar-like member 31 can fit into vertical space 33 between wings 37, 39 (and over the archwire 34) of a common bracket 32. The integral bar member 31 may also have a hook-like tail 41 extending therefrom to better hold a rubber band. A similar arrangement may also be used on any other tooth (e.g., a lower tooth) to attach the other end of the rubber band for reciprocal force. The bar member serves generally three purposes; first to anchor the ring against movement or rotation to the forces on the rubber band, second to provide structural support for the attachment of one or more rubber bands to extension 41, and third, by virtue of its placement over the archwire 34, to help retain the archwire in the bracket slot 35.

It is preferred that the O-ring portion 11 of the ligature 10, comprising the inner and outer portions 12, 14 be constructed of an stretchable plastic material and that the preferably integral arm 18 be constructed of a semi-rigid material. The O-ring 11 can thus be stretched as needed in use, but the arm 18 can provide adequate retention of other elements as needed in use. The material currently preferred is Adipic Acid-Bis(4-Isocyanatophenyl) Methane-1,4-Butanediol Polymer. However, any suitable material may be used, including virgin or recycled polyolefins, polyethylene (PE), polyvinyl chloride (PVC), acrylonitrile butadiene (ABS), styrene plastics, polypropylene, polyamides (PA), and polycarbonates (PC) or ultrahigh molecular weight high-density polyethylene (HDPE-UHMW). Polypropylene homopolymer, or polypropylene block copolymer may also be used. Another material may be selected from among the polyolefins containing materials like LLDPE, TPE, EVA, EEA and the like.

Figure 4:
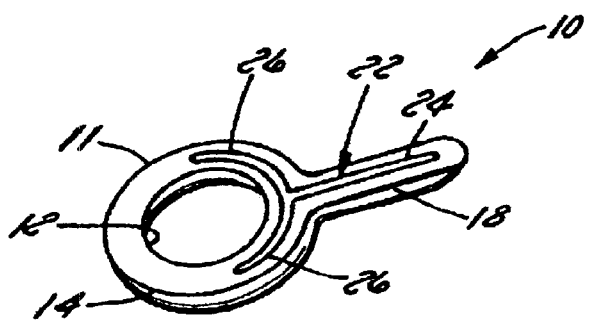
FIG. 4 illustrates a partially cut away, perspective view of another embodiment of the invention.

The O-ring 11 and arm 18 may thus be comprised of two or more different materials molded together in a single unit, may be comprised of two or more different component parts molded within a single exterior unit, or may be comprised of two or more materials arranged in layers. For example, as seen in FIG. 4, one embodiment of the ligature 10 contemplates the insertion of a wire 22 within ligature 10. The wire 22 would provide rigidity to the arm portion 18 of the ligature 10 via the arm portion 24 and would connect with the body 11 of the ligature 10 via body portions 26 without sacrificing the elasticity of the body 11. While the ligature of FIG. 4 comprises different materials, the materials are molded together in a single ligature 10 so that the orthodontist is provided with a ligature requiring a single step but providing dual uses.

The wire 22 could as easily be a piece of plastic or other-material that would lend rigidity to the arm 18 without adversely affecting the elasticity of the body 11. Another manufacturing solution may be the addition of layer of plastic or other suitable material over the arm 18 so that the elastic material used in the O-ring 11 would form the "backbone" of the arm 18 but would achieve the requisite rigidity by way of an "exoskeleton".

3. In Use and Operation

A common orthodontic system and novel device to be used therewith has been described above and is shown in FIG. 3. In use, the orthodontist typically attaches a series of upper and lower brackets 32, 42 to a patient's upper and lower teeth 30, 40, positions upper and lower archwires 34, 44 through consecutive brackets 32, 42, and holds the archwires 34, 44 on the brackets 32, 42 with a ligature 10. The ligature 10 is of the type described herein and thus bears an integral arm 18, hook, or other retaining member. Connectors such as elastic bands 50, may be provided between two or more upper and/or lower brackets 32, 42 via the retaining members of ligatures 10 to effect tooth movement in a desired direction.

In the inventive method, the orthodontist secures the archwires 34, 44 to selected brackets 32, 42 applying the ligature 10 in the same manner in which standard ligatures 29 are applied. He or she is then able to attach a first end 52 of a connector or elastic band 50 from the retaining arm 18 of a ligature 10 around an upper bracket 32, for example, and pull the elastic band 50 so that its second end 54 is attached to the retaining arm 18 of a ligature 10 placed around a lower bracket 42, as seen in FIG. 3.

The orthodontist will need to make certain observations before installing the novel ligatures 10. First, he or she will want to secure the ligature 10 so that the arm 18 is best able to attach other elements. The retaining arm 18 should thus be placed so that it will be aligned with the directional pull D of the elastic band 50 to be attached for the most secure retention of the elastic band 50 on the arm 18. Second, in order to prevent rotation of the properly placed ligature 10 about the bracket 32, 42, projections 15 as described above (in FIGS. 1 & 2) may be provided within the ligature 10. When projections 15 are present, especially of a unidirectional type 16 that grip the bracket 32, 42 against forces in the opposite direction, the ligature 10 becomes "sided" so that the orthodontist must flip the ligature 10 to the proper side in order to obtain the proper gripping action.

Figure 3:
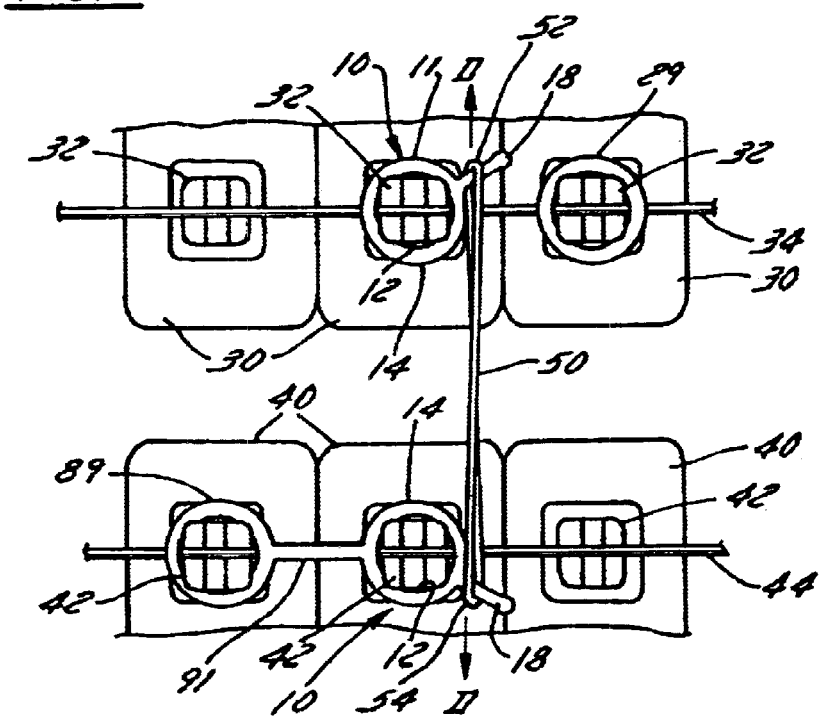
FIG. 3 illustrates a view of an embodiment of the invention in use in an orthodontic assembly.

As with traditional ligatures, the inventive ligature 10 may be linked in a chain with one or more conventional ligatures 89 via a link 91 to keep spacing of teeth proper (see FIG. 3). Of course, a multitude of inventive ligatures could also be linked in the same fashion for the same purpose.

Of course, as is known in the art, pairs or groups of upper teeth 30 and their brackets 32 may be attached together using the above-described inventive method. Similarly, pairs or groups of lower teeth 40 and their brackets 42 may be attached together by this same method.

Although the best mode contemplated by the inventor of carrying out the method of the present invention is disclosed above, practice of the present invention is not limited thereto. It will be manifest that various additions, modifications and rearrangements of the features of the present invention may be made without deviating from the spirit and scope of the underlying inventive concept.

For example, the ligature could be enhanced by providing it in anti-bacterial materials, in various colors and sizes, and on a variety of dispensers. Similarly, although the O-ring disclosed herein has a generally flat shape, the ligature 10 could be provided with a curved profile for advantageous attachment of the ligature to the bracket, as seen in FIG. 9.

Furthermore, all the disclosed features of each disclosed embodiment can be combined with, or substituted for, the disclosed features of every other disclosed embodiment except where such features are mutually exclusive. For example, a ligature 10 of the present invention could comprise the retaining head 20 shown in FIG. 1, the projections 15 shown in FIG. 2, and one or both of the angles illustrated in FIGS. 4–7. Further, the angle of the retaining arm 18 may vary based on the intended application. It is intended that the appended claims cover all such additions, modifications and rearrangements. Expedient embodiments of the present invention are differentiated by the appended subclaims.

I claim:

1. A device for use with an orthodontic bracket comprising a ligature having:
   (A) a body, wherein the body has an interior portion and an exterior portion; and
   (B) a retaining arm projecting from the exterior portion, wherein the arm comprises a generally spherical second portion at the distal end of the first portion.

2. The device of claim 1, wherein the arm is planar with the body.

3. The device of claim 1, wherein the arm is angled away from the plane of the body.

4. The device of claim 1, wherein the arm extends from the exterior portion at about a 90 degree angle.

5. The device of claim 1, wherein the arm extends from the exterior portion at an angle other than 90 degrees.

6. The device of claim 1, wherein the interior portion has at least one projection to prevent rotation of the ligature about the bracket.

7. The device of claim 1, further comprising a plurality of unidirectional barbs in the interior portion.

8. The device of claim 1 wherein the ligature is round and has a bar-like member through the center which fits between wings of a bracket and is integral with the arm.

9. A device for use with all orthodontic bracket comprising a ligature having:
   (A) a body, wherein the body has an interior portion and an exterior portion; and
   (B) a retaining arm projecting from the exterior portion, wherein a rigid structure is embedded within the arm.

10. The device of claim 9, wherein the arm is generally cylindrical.

11. The device of claim 9, wherein the arm comprises a generally cylindrical first portion.

12. The device of claim 9, wherein the arm is made of a different material than the interior and exterior portions of the ligature.

13. The device of claim 9, further comprising a means for preventing rotation of the ligature about the bracket.

14. The device of claim 9 wherein the ligature is round and has a bar-like member through the center which fits between wings of a bracket and is integral with the arm.

15. The device of claim 9, wherein the arm extends from the exterior portion at an angle other than 90 degrees.

16. The device of claim 9, further comprising a plurality of unidirectional barbs in the interior portion.

17. An orthodontic assembly comprising:
   (A) a multiplicity of brackets for attachment to the teeth of a patient;
   (B) an archwire for serial attachment of the brackets;
   (C) a multiplicity of ligatures for connecting the archwire to the brackets, wherein at least two of the ligatures further comprise an integral retaining arm; and
   (D) at least one connector for moving at least one tooth in relation to at least one other tooth, wherein said connector is retained by the retaining arms of the at least two ligatures.

18. The assembly of claim 17, wherein the retaining arm is formed of a different material than the ligature.

19. The assembly of claim 18, wherein the material of the retaining arm is generally rigid and the material of the ligature is generally elastic.

20. An orthodontic method comprising:
   (A) attaching a bracket to a tooth of a patient;
   (B) positioning an archwire in the bracket;
   (C) securing the archwire to the bracket with a device including an O-shaped body having a plurality of interior projections and an integral retaining arm extending from the body;
   (D) placing a first end of a connector over the retaining arm adjacent a first tooth; and
   (E) placing a second end of the connector over the retaining arm adjacent a second tooth.

21. The method of claim 20, wherein the step of securing comprises turning the device so that the integral retaining arm is angled away from the direction in which the connector will pull.

22. The method of claim 18, wherein the step of securing comprises flipping the device so that the interior projections prevent the body and arm from rotating in the direction in which the connector will pull.

23. An orthodontic ligature used to connect an archwire to a bracket the improvement comprising a semi-rigid arm extending from the ligature, wherein the rigidity of the arm is created by a structure embedded within the arm.

24. The improvement of claim 23, wherein the arm is connected to the ligature.

25. The improvement of claim 23, wherein the arm is integral with the ligature.

26. The improvement of claim 23, wherein the arm is formed of a different material than the ligature.

* * * * *